United States Patent
Battu et al.

(10) Patent No.: US 11,273,128 B1
(45) Date of Patent: Mar. 15, 2022

(54) ELAGOLIX FORMULATION

(71) Applicant: Sandoz AG, Basel (CH)

(72) Inventors: Vivek Battu, Hyderabad (IN); Akash Vijay Lingayat, Hyderabad (IN); Amit Gupta, Hyderabad (IN); Anandkrishna Laxmikant Kulkanri, Hyderabad (IN)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 17/231,118

(22) Filed: Apr. 15, 2021

(51) Int. Cl.
*A61K 9/20* (2006.01)
*A61K 33/08* (2006.01)
*A61K 31/506* (2006.01)
*A61K 9/00* (2006.01)

(52) U.S. Cl.
CPC .......... *A61K 9/2095* (2013.01); *A61K 9/0053* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 31/506* (2013.01); *A61K 33/08* (2013.01)

(58) Field of Classification Search
None
See application file for complete search history.

(56) References Cited

U.S. PATENT DOCUMENTS 3,857,939 A * 12/1974 Green ............... A61K 9/0056
424/692
2002/0013357 A1 * 1/2002 Nadkarni ........... A61K 2300/00
514/406

FOREIGN PATENT DOCUMENTS

| EP | 3572406 A1 | 11/2019 |
| WO | 2018189212 A1 | 10/2018 |
| WO | 2018189213 A1 | 10/2018 |
| WO | 2019036712 A1 | 2/2019 |
| WO | 2020020999 A1 | 1/2020 |
| WO | 2020043763 A1 | 3/2020 |

OTHER PUBLICATIONS

ICH Harmonized Guideline, Impurities: Guidelines for residual solvents Q3C(R6), final version, adopted on Oct. 20, 2016.

* cited by examiner

*Primary Examiner* — Aradhana Sasan
(74) *Attorney, Agent, or Firm* — Luedeka Neely Group, P.C.

(57) ABSTRACT

A pharmaceutical formulation is disclosed which includes at least: (1) elagolix sodium, (2) magnesium oxide, and (3) at least one disintegrating agent, such as crospovidone, croscarmellose sodium, sodium starch glycolate, pregelatinized and mixtures thereof. A tablet is also disclosed which includes a tablet core formed from the pharmaceutical formulation. The elagolix sodium tablets of the present disclosure display improved dissolution rates when tested using for example the Tablet Sink Time test. The tablets also exhibit improved storage stability of the elagolix sodium, with a reduction in degradation products during storage.

16 Claims, 2 Drawing Sheets

ELAGOLIX FORMULATION

FIELD

The present disclosure relates to pharmaceutical formulations including elagolix sodium, together with magnesium oxide and at least one disintegrating agent. The disclosure also relates to tablet dosage forms incorporating this pharmaceutical formulation, having improved dissolution rates and improved storage stability, and to methods for preparation of such tablets.

BACKGROUND

Elagolix is an orally available gonadotropin-releasing hormone (GnRH) receptor antagonist indicated for the treatment of endometriosis and uterine fibroids. The chemical name of elagolix is 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1 (2H)-pyrimidinyl]-1-phenylethyl]amino]butanoic acid. Elagolix is an uracil derivative which can be represented by the chemical structure according to Formula (I)

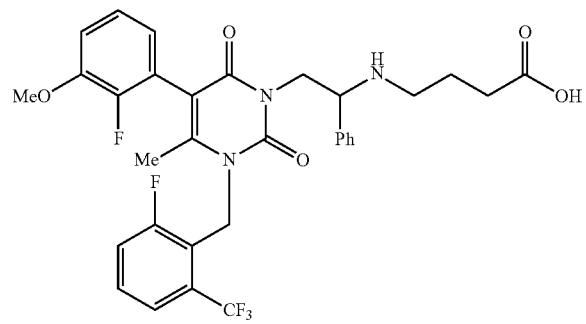 [SMILES: COc1cccc(-c2c(C)n(Cc3c(F)cccc3C(F)(F)F)c(=O)n(CC(NCCCC(=O)O)c3ccccc3)c2=O)c1F]

(I) (elagolix free acid), wherein the R-form Ia is preferred:

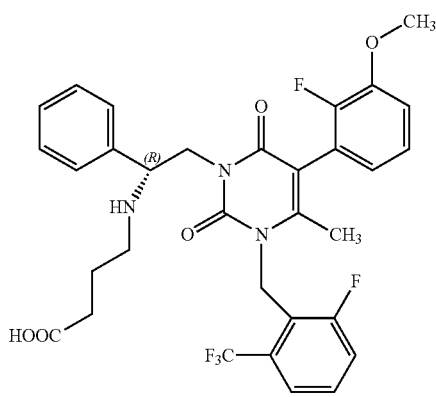

(Ia) (elagolix free acid, R-form).

Elagolix may be administered in the form of various pharmaceutically acceptable salts, including in particular elagolix sodium which can be represented by the chemical structure according to Formula (II)

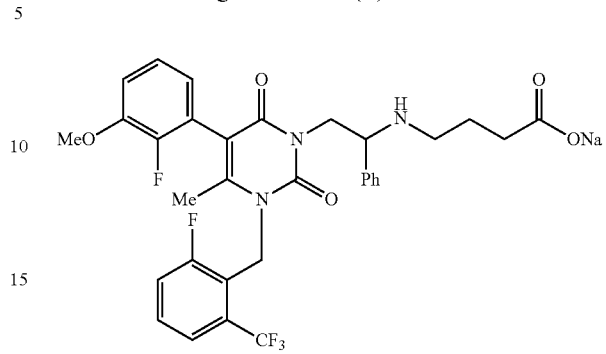

(II) (elagolix sodium), wherein the R-form IIa is preferred:

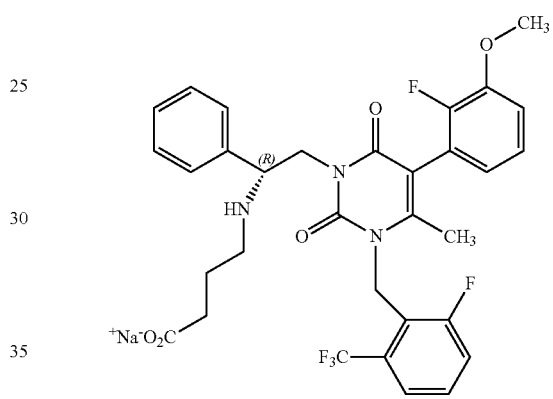

(IIa) (elagolix sodium, R-form).

Elagolix is known to be unstable and susceptible to degradation during long term storage, leading to the formation of a lactam impurity within pharmaceutical dosage forms incorporating elagolix. In addition, elagolix may in some dosage forms exhibit relatively slow dissolution rates, leading to unacceptably slow release of the active ingredient when taken by the patient.

Previously, WO2019/036712 describes an elagolix formulation containing a so-called anti-gelling agent and at least 10% Compound A (elagolix). According to the reference, the anti-gelling agent may be a water-soluble salt of a weak acid, a base, a basic amino acid, a basic salt or a basic polymer, and the anti-gelling agent further acts as a stabilizer to reduce formation of a degradation product called Compound B. The reference principally focuses on sodium carbonate as the anti-gelling/stabilizing agent.

Additionally, WO2018/189213 discloses elagolix in the form of a solid dispersion which includes the elagolix together with at least one silicon-based inorganic compound.

WO2018/189212 discloses acid addition salts of elagolix with strong acids such as sulfuric acid and hydrochloric acid and pharmaceutical compositions including such elagolix acid addition salts. Similarly, EP 3572406 discloses methods for preparing acid addition salts of elagolix, along with pharmaceutical compositions incorporating the acid addition salts.

Further, WO2020/043763 discloses a method for preparation of a powder comprising elagolix by providing a solution containing elagolix, combining the solution with an insoluble, crystalline filler, and spray drying this suspension.

Finally, WO 2020/020999 discloses a process for preparing rapidly or very rapidly dissolving tablets comprising freely soluble active pharmaceutical ingredients, such as for example elagolix.

Despite the aforementioned disclosures, difficulties remain in providing satisfactory elagolix dosage forms. Thus, there remains a continuing need for elagolix dosage forms having improved dissolution rates and improved storage stability, and for methods for preparation of such dosage forms.

SUMMARY OF THE INVENTION

The above and other needs are met by a pharmaceutical formulation according to the present disclosure.

Thus, in a first aspect, the present disclosure provides a pharmaceutical formulation. According to one embodiment, this pharmaceutical formulation includes at least: (1) elagolix sodium, (2) magnesium oxide, and (3) at least one disintegrating agent.

In certain embodiments, the pharmaceutical formulation preferably includes from about 20 weight percent to about 50 weight percent of the elagolix sodium, based on the total weight of the formulation. More preferably, the pharmaceutical formulation includes from about 30 weight percent to about 40 weight percent of the elagolix sodium, based on the total weight of the formulation.

In some embodiments, the pharmaceutical formulation preferably includes from about 10 weight percent to about 25 weight percent of the magnesium oxide, based on the total weight of the formulation. More preferably, the pharmaceutical formulation includes from about 15 weight percent to about 20 weight percent of the magnesium oxide, based on the total weight of the formulation.

In some instances, the pharmaceutical formulation also includes at least one disintegrating agent. Preferably, the at least one disintegrating agent is selected from the group consisting of crospovidone, croscarmellose sodium, sodium starch glycollate, pregelatinized starch, and mixtures thereof. More preferably, according to certain embodiments, the pharmaceutical formulation may include crospovidone, sodium starch glycollate, and pregelatinized starch.

In accordance with some embodiments, the pharmaceutical formulation preferably includes from about 15 to about 40 weight percent of the at least one disintegrating agent based on the total weight of the formulation. More preferably, the pharmaceutical formulation preferably includes from about 15 to about 30 weight percent of the at least one disintegrating agent based on the total weight of the formulation.

In addition to the (1) elagolix sodium, (2) magnesium oxide, and (3) at least one disintegrating agent, the pharmaceutical formulation may also include additional excipients. For instance, in certain embodiments, the pharmaceutical formulation preferably also includes at least one excipient selected from the group consisting of sugar alcohols, cellulose derivatives, silica, binders, and lubricants. Preferably, the pharmaceutical formulation further comprises one or more sugar alcohols, such as pentoses or hexoses or sugar alcohols with 12 carbon atoms, such as xylitol, mannitol, arabitol, galactitol, isomalt, maltitol or lactitol, most preferably mannitol. More particularly, the pharmaceutical formulation preferably also includes at least one excipient selected from the group consisting of mannitol, low substituted hydroxypropyl cellulose, colloidal silica, povidone, and magnesium stearate.

In a second aspect, the present disclosure provides an oral dosage form, such as a tablet for instance. This oral dosage form includes a pharmaceutical formulation such as the formulation described above, i.e., a formulation which includes at least: (1) elagolix sodium, (2) magnesium oxide, and (3) at least one disintegrating agent.

According to one embodiment, the present disclosure provides a tablet which includes a tablet core, and a coating layer applied over the tablet core. The tablet core, in turn, includes a pharmaceutical formulation which includes at least: (1) elagolix sodium, (2) magnesium oxide, and (3) at least one disintegrating agent.

In accordance with some embodiments, the amount of the active ingredient elagolix sodium in the tablet is preferably from about 140 mg to about 315 mg of elagolix, in the form of elagolix sodium.

In general, tablets according to the present disclosure have been found to exhibit excellent dissolution rates when subjected to dissolution testing. According to certain embodiments, the tablet preferably has a Tablet Sink Time of about 35 minutes or less when measured in a 0.1 M HCl at a pH of about 1.2 in accordance with United States Pharmacopeia (USP) Chapter 701 (Disintegration).

In certain embodiments, at least 75 percent of the elagolix sodium is preferably released from the tablet within 45 minutes when subjected to dissolution testing in a 0.05 M phosphate buffered dissolution solution at a pH of about 6.8.

Additionally, according to certain embodiments, at least 75 percent of the elagolix sodium is preferably released from the tablet within 45 minutes when subjected to dissolution testing in a 0.1 M HCl at a pH of about 1.2.

The tablets according to the present disclosure have also been found to exhibit improved storage stability of the elagolix sodium active ingredient, so that conversion of the elagolix sodium to degradation products during storage is reduced. For instance, according to certain embodiments, the tablet of the present disclosure has been found to include less than about 0.1 weight percent of an elagolix sodium degradation product according to Formula (III)

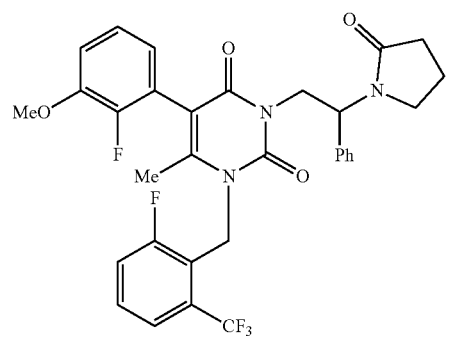

(III), in particular the R-form:

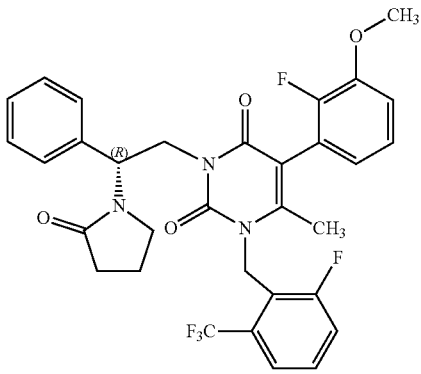

(IIIa) (R-form).

when measured after storage of the tablet for a period of 3 months at a temperature of about 40° C. and at about 75 percent relative humidity.

Also, in certain embodiments, the tablet of the present disclosure has been found to include less than about 0.2 weight percent of an elagolix sodium degradation product according to Formula (III)

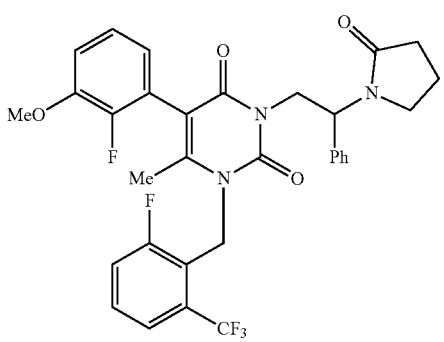

(III), in particular the R-form:

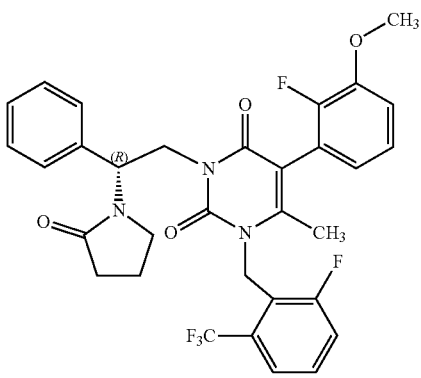

(IIIa) (R-form)

when measured after storage of the tablet for a period of 6 months at a temperature of about 40° C. and at about 75 percent relative humidity.

In a further aspect, the present disclosure also provides methods for preparing a tablet core.

According to one embodiment, a method for preparing a tablet core includes a first step of mixing elagolix sodium, magnesium oxide, at least one disintegrating agent, and optionally at least one additional excipient to provide a tableting mixture; a second step of forming a tablet core by direct compression of the tableting mixture; and a third optional step of film-coating the tablet core.

According to another embodiment, a method for preparing a tablet core includes a first step of preparing a granulation mixture which includes elagolix sodium, magnesium oxide, at least one disintegrating agent, and optionally at least one additional excipient. The method also includes a second step of blending the granulation mixture with an extragranular composition which includes at least a lubricant and disintegrant, to provide a tableting mixture. The method also includes a third step of forming a tablet core from the tableting mixture. The method also includes a fourth optional step of film-coating the tablet core. In some instances, the granulation mixture is preferably prepared in a water-free process.

In still another aspect, the present disclosure provides a use of a pharmaceutical formulation as disclosed above, or an oral dosage form or a tablet including the pharmaceutical formulation, for treating endometriosis-associated pain or uterine fibroids.

The present disclosure also provides a method of treatment of patient suffering from endometriosis-associated pain or uterine fibroids by administering to the patient an effective dose of a pharmaceutical formulation as disclosed above, or an oral dosage form or a tablet including the pharmaceutical formulation.

BRIEF DESCRIPTION OF THE DRAWINGS

Further advantages of the disclosure are apparent by reference to the detailed description when considered in conjunction with the figures, wherein.

DETAILED DESCRIPTION

Figure 1:
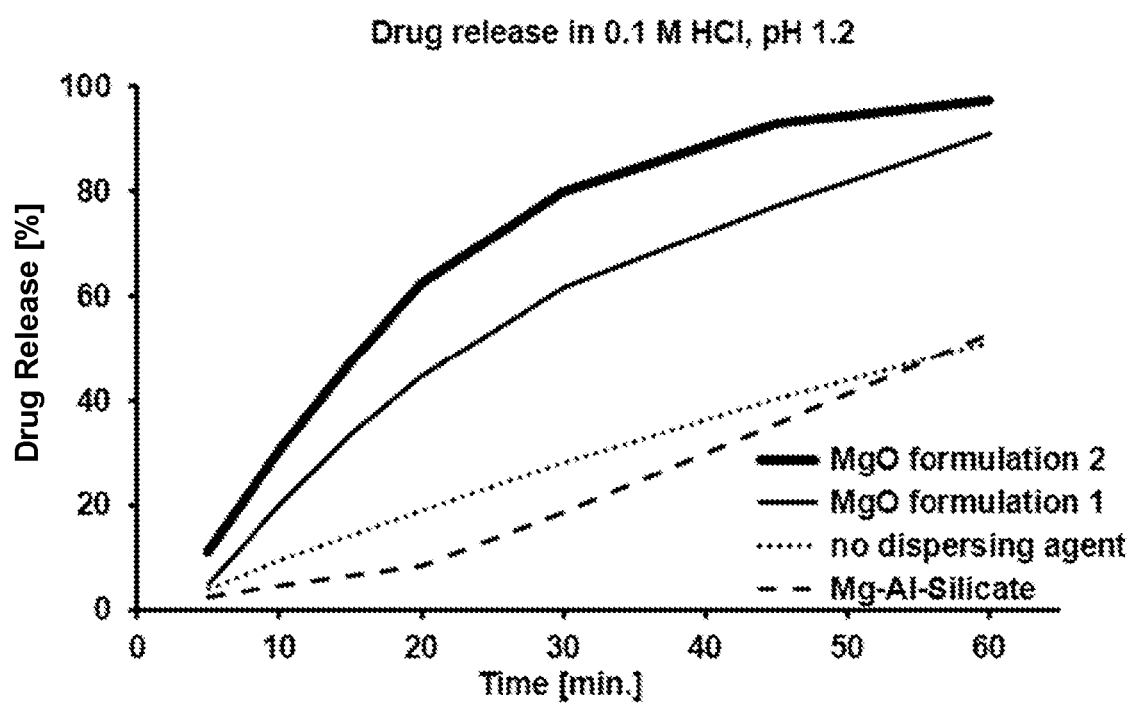
FIG. 1 illustrates the drug release in 0.1 M HCl, pH 1.2.

According to the present disclosure, an elagolix sodium pharmaceutical formulation is provided. This formulation may be prepared in the form of tablets having improved dissolution rates as well as improved long term storage stability.

The pharmaceutical formulation of the present disclosure may be used for the treatment of endometriosis-associated pain or uterine fibroids.

According to one embodiment, the pharmaceutical formulation according to the present disclosure includes at least components: (1) elagolix sodium, (2) magnesium oxide, and (3) at least one disintegrating agent.

The active ingredient of the formulation, elagolix sodium, may be represented by the chemical structure according to Formula (II)

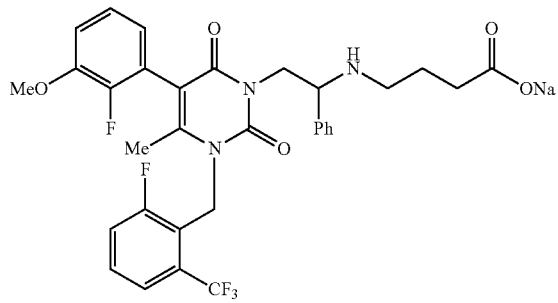

(II) (elagolix sodium), wherein the R-form IIa is preferred:

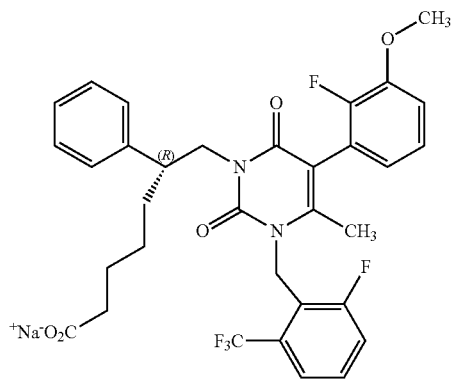

(IIa) (elagolix sodium, R-form).

Elagolix sodium principally found in amorphous form. Thus, the elagolix sodium of the pharmaceutical formulation is typically of amorphous form. In general, at least 80 weight percent of the elagolix sodium used in the pharmaceutical formulation is in amorphous form. More preferably at least 90 weight percent of the elagolix sodium used in the pharmaceutical formulation is in amorphous form.

The amount of this elagolix sodium in the pharmaceutical formulation is typically from about 20 weight percent to about 50 weight percent, based on the total weight of the formulation. More preferably, the pharmaceutical formulation includes from about 30 weight percent to about 40 weight percent of the elagolix sodium, based on the total weight of the formulation.

In addition to the elagolix sodium active ingredient, the pharmaceutical formulation also includes magnesium oxide (MgO). As used herein, "magnesium oxide" refers to MgO and does not include hydroxide of magnesium such as $Mg(OH)_2$.

Without being bound by theory, the magnesium oxide is believed to function as a dispersing agent within the formulation to improve the dispersion of the active ingredient when ingested by the patient.

The amount of this magnesium oxide in the pharmaceutical formulation is typically from about 10 weight percent to about 25 weight percent, based on the total weight of the formulation. More preferably, the pharmaceutical formulation includes from about 15 weight percent to about 20 weight percent of the magnesium oxide, based on the total weight of the formulation.

In general, the pharmaceutical formulation also includes at least one disintegrating agent together with the elagolix sodium and the magnesium oxide. Preferably, the at least one disintegrating agent is selected from the group consisting of crospovidone, croscarmellose sodium, sodium starch glycollate, pregelatinized starch, and mixtures thereof. More preferably, according to certain embodiments, the pharmaceutical formulation may include a combination of crospovidone, sodium starch glycollate, and pregelatinized starch.

The overall amount of the disintegrating agent in the formulation is typically from about 15 to about 40 weight percent, based on the total weight of the formulation. More preferably, the disintegrating agent in the formulation is typically from about 15 to about 30 weight percent, based on the total weight of the formulation.

In instances in which multiple disintegrating agents are used in combination within the pharmaceutical formulation such crospovidone, sodium starch glycollate, and pregelatinized starch, the amount of crospovidone is preferably from about 10 to about 20 weight percent, based on the total weight of the formulation, the amount of sodium starch glycollate is preferably from about 2 to about 5 weight percent, based on the total weight of the formulation, and the amount of pregelatinized starch is preferably from about 3 to about 10 weight percent, based on the total weight of the formulation.

In addition to the (1) elagolix sodium, (2) magnesium oxide, and (3) at least one disintegrating agent, the pharmaceutical formulation may also include additional excipients. For instance, in certain embodiments, the pharmaceutical formulation preferably also includes at least one excipient selected from the group consisting of sugar alcohols, cellulose derivatives, silica, binders, and lubricants. More particularly, the pharmaceutical formulation preferably also includes at least one excipient selected from the group consisting of mannitol, low substituted hydroxypropyl cellulose, colloidal silica, povidone, and magnesium stearate.

The foregoing elagolix sodium formulation is provided as an oral dosage form in accordance with a second aspect of the present disclosure. For instance, the elagolix sodium pharmaceutical formulation may be provided as a tablet or a capsule. Preferably, the elagolix sodium pharmaceutical formulation is provided as a tablet.

This tablet according to the present disclosure typically includes the active ingredient elagolix in the tablet in an amount from about 140 mg to about 315 mg of elagolix, in the form of elagolix sodium. For instance, in one embodiment, the tablet may include about 150 mg of elagolix, in the form of elagolix sodium. In a different embodiment, the tablet may include about 200 mg of elagolix, in the form of elagolix sodium. In still another embodiment, the tablet may include about 300 mg of elagolix, in the form of elagolix sodium. 150 mg elagolix corresponds to 155.2 mg elagolix sodium, 200 mg elagolix corresponds to 207 mg elagolix sodium, and 300 mg elagolix corresponds to 310.4 mg elagolix sodium.

According to the present disclosure, the tablet includes at least a tablet core. The tablet, in turn, includes an intragranular portion which is made up of the pharmaceutical formulation. Thus, the intragranular portion includes at least: elagolix sodium, magnesium oxide, at least one disintegrating agent, and possibly additional excipients.

In some embodiments, the tablet core may also include an extragranular portion which is blended with the granulate prior to pressing of the tablet core. If present, this extragranular portion preferably includes additional disintegrating agent and a lubricant. For instance, the extragranular portion may include a disintegrating agent such as crospovidone and a lubricant such as magnesium stearate.

In many instances, a coating layer will also be applied over the tablet core to provide the final tablet. For instance, a coating of a film forming material may be applied over the tablet core. Preferably the film forming coating is an immediate release film coating, and the release rate of the film coating is independent of environmental pH. An example of a suitable film coating is Colorcon Opradry films coatings.

The present disclosure also provides methods for preparing a tablet core.

According to one embodiment, a method for preparing a tablet core includes a first step of mixing elagolix sodium, magnesium oxide, at least one disintegrating agent to provide a tableting mixture. Optionally, the tableting mixture may also include one or more additional excipients. In a second step, this tableting mixture is formed into a tablet core by direction compression of the mixture, such as in a tableting press.

In an alternative embodiment, a method for preparing a tablet core includes a first step of preparing a granulation mixture which includes elagolix sodium, magnesium oxide, at least one disintegrating agent, and optionally at least one additional excipient. The method then includes a second step of blending the granulation mixture with an extragranular composition which includes at least a lubricant, to provide a tableting mixture. In some instances, the extragranular composition may include additional disintegrating agent and/or additional excipients. The method also includes a step of forming a tablet core from the tableting mixture.

The preparation of the granulation mixture may be carried out by dry granulation, wet granulation, or by fluid bed granulation. If a wet granulation is carried out, the granulating liquid may be water, or non-aqueous solvent(s), or a mixture of water and non-aqueous solvent(s). In some instances, the granulating liquid comprises non-aqueous solvent(s) and is water-free.

In certain embodiments, tablet is preferably prepared using a wet granulation method, wherein the granulating liquid comprises non-aqueous solvent(s) and is water-free. Preferred non-aqueous solvents include dichloromethane, ethanol, isopropanol, acetone, and mixtures thereof, more preferably the non-aqueous solvents include acetone and dichloromethane, and mixtures thereof. Dichloromethane is a Class 2 solvent, and acetone is a Class 3 solvent, as per ICH Harmonized Guideline, Impurities: Guidelines for residual solvents Q3C(R6), final version, adopted on 20 Oct. 2016 (https://database.ich.org/sites/default/files/Q3C-R6_Guideline_ErrorCorrection_2019_0410_0.pdf). Under point 3.1 the ICH Guideline above characterizes Class 1 solvents as solvents to be avoided, Class 2 solvents as solvents to be limited, and Class 3 solvents as solvents with low toxic potential to human health. Hence, most preferably, the non-aqueous solvent is acetone (=Class 3 solvent).

In certain embodiments, if a tablet is prepared using wet granulation, magnesium oxide is dispersed in water and granulated. Then, the obtained wet mass is dried and screened through an appropriate screen. To the screened granules, elagolix sodium (the API, active pharmaceutical ingredient) and other excipients are added and compressed. An example of such an embodiment is Example 4A.

In certain embodiments, if a tablet is prepared using wet granulation, Potassium hydroxide or Meglumine or Magnesium aluminum silicate is dispersed in water and granulated. Then, the wet mass is dried and screened through an appropriate screen. To the screened granules, elagolix sodium and the further excipients are added and compressed. An example of such an embodiment is Example 4B.

In certain embodiments, which are the preferred embodiments, if a tablet is prepared by using wet granulation, Magnesium oxide including the API elagolix sodium and other excipients are granulated with acetone, dichloromethane, or isopropanol. Then, the wet mass is dried and screened through an appropriate screen. To the screened granules, the other excipients are added and compressed. An example of such an embodiment is Example 4C.

In other embodiments, the tablet is preferably prepared by direct compression.

The pharmaceutical formulation according to the present disclosure is suitable for the treatment of endometriosis-associated pain or uterine fibroids. Accordingly, the present disclosure also provides a use of a pharmaceutical formulation as disclosed above, or an oral dosage form or a tablet comprising the pharmaceutical formulation, for treating endometriosis-associated pain or uterine fibroids.

The present disclosure also provides a method of treatment of patient suffering from endometriosis-associated pain or uterine fibroids by administering to the patient an effective dose of a pharmaceutical formulation as disclosed above, or an oral dosage form or a tablet comprising the pharmaceutical formulation.

The aforementioned tablets according to the present disclosure have also been found to exhibit good disintegration rates. According to certain embodiments, the tablet preferably has a Tablet Sink Time of about 35 minutes or less when measured in a 0.1 M HCl at a pH of about 1.2 in accordance with United States Pharmacopeia (USP) Chapter 701 (Disintegration).

Moreover, in dissolution testing, it was found that at least 75 percent of the elagolix sodium is preferably released from the tablet within 45 minutes when subjected to dissolution testing in a 0.05 M phosphate buffer at a pH of about 6.8.

Further, according to certain embodiments, at least 75 percent of the elagolix sodium is preferably released from the tablet within 45 minutes when subjected to dissolution testing in a 0.1 M HCl at a pH of about 1.2.

The tablets according to the present disclosure have also been found to exhibit improved storage stability of the elagolix sodium active ingredient, so that conversion of the elagolix sodium to degradation products during storage is reduced. For instance, according to certain embodiments, the tablet of the present disclosure has been found to include less than about 0.1 weight percent of an elagolix sodium degradation product according to Formula (III)

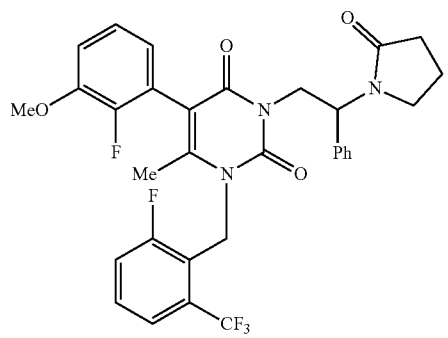 [SMILES: COc1cccc(-c2c(C)n(Cc3c(F)cccc3C(F)(F)F)c(=O)n(CC(c3ccccc3)N3CCCC3=O)c2=O)c1F]

(III), in particular the R-form:

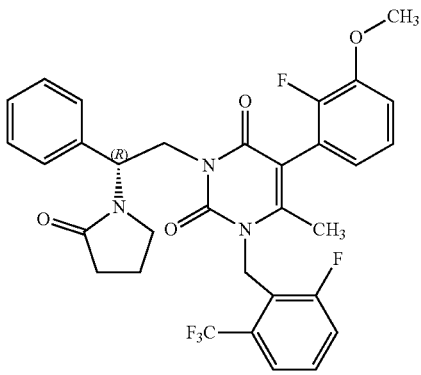

(IIIa) (R-form) when measured after storage of the tablet for a period of 3 months at a temperature of about 40° C. and at about 75 percent relative humidity.

Also, in certain embodiments, the tablet of the present disclosure has been found to include less than about 0.2 weight percent of an elagolix sodium degradation product according to Formula (III)

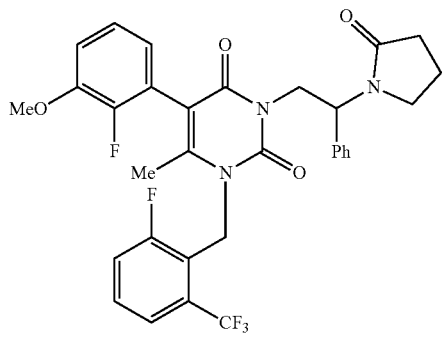 [SMILES: COc1cccc(-c2c(C)n(Cc3c(F)cccc3C(F)(F)F)c(=O)n(CC(c3ccccc3)N3CCCC3=O)c2=O)c1F]

(III), in particular the R-form:

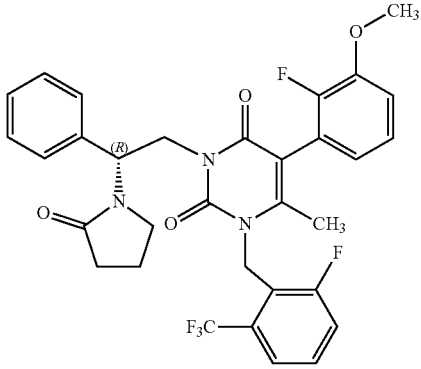

(IIIa) (R-form)
when measured after storage of the tablet for a period of 6 months at a temperature of about 40° C. and at about 75 percent relative humidity.

The present disclosure is also further illustrated by the following embodiments:

Embodiment 1. A pharmaceutical formulation comprising: elagolix sodium; magnesium oxide; and at least one disintegrating agent.

Embodiment 2. The pharmaceutical formulation of Embodiment 1, wherein the formulation comprises from about 20 weight percent to about 50 weight percent of the elagolix sodium, more preferably from about 30 weight percent to about 40 weight percent of the elagolix sodium, based on the total weight of the formulation.

Embodiment 3. The pharmaceutical formulation of Embodiment 1 or 2, wherein the formulation comprises from about 10 weight percent to about 25 weight percent of the magnesium oxide, more preferably from about 15 weight percent to about 20 weight percent of the magnesium oxide, based on the total weight of the formulation.

Embodiment 4. The pharmaceutical formulation of any of Embodiments 1-3, wherein the formulation comprises at least one disintegrating agent selected from the group consisting of crospovidone, croscarmellose sodium, sodium starch glycollate, pregelatinized starch, and mixtures thereof.

Embodiment 5. The pharmaceutical formulation of any of Embodiments 1-4, wherein the formulation comprises from about 15 to about 40 weight percent, preferably from about 15 to about 30 weight percent, of the at least one disintegrating agent based on the total weight of the formulation.

Embodiment 6. The pharmaceutical formulation of any of Embodiments 1-5, wherein the formulation comprises crospovidone, sodium starch glycolate, and pregelatinized starch.

Embodiment 7. The pharmaceutical formulation of any of Embodiments 1-6, wherein the formulation further comprises at least one excipient selected from the group consisting of sugar alcohols, cellulose derivatives, silica, binders, and lubricants.

Embodiment 8. The pharmaceutical formulation of any of Embodiments 1-7, wherein the formulation further comprises at least one excipient selected from the group consisting of low substituted hydroxypropyl cellulose, colloidal silica, povidone, and magnesium stearate, and/or wherein, the pharmaceutical formulation further comprises one or more sugar alcohols, such as pentoses or hexoses or sugar alcohols with 12 carbon atoms, such as xylitol, mannitol, arabitol, galactitol, isomalt, maltitol or lactitol, most preferably mannitol.

Embodiment 9. An oral dosage form comprising the pharmaceutical formulation of any of Embodiments 1-8.

Embodiment 10. A tablet comprising a tablet core, which comprises the pharmaceutical formulation of any of Embodiments 1-8; and a coating layer applied over the tablet core.

Embodiment 11. The tablet of Embodiment 10, wherein the tablet comprises from about 140 mg to about 315 mg of elagolix sodium, in the form of elagolix sodium.

Embodiment 12. The tablet of Embodiment 10 or 11, wherein the tablet has a Tablet Sink Time of about 35 minutes or less when measured in a 0.1 M HCl at a pH of about 1.2 in accordance with USP Chapter 701 (Disintegration).

Embodiment 13. The tablet of any of Embodiments 10-12, wherein the tablet comprises less than about 0.1 weight percent of an elagolix sodium degradation product according to Formula (III)

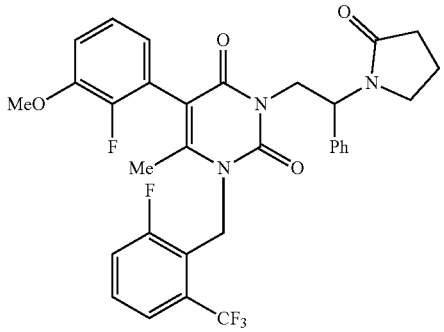 [SMILES: COc1cccc(-c2c(C)n(Cc3c(F)cccc3C(F)(F)F)c(=O)n(CC(c3ccccc3)N3CCCC3=O)c2=O)c1F]

(III), in particular the R-form:

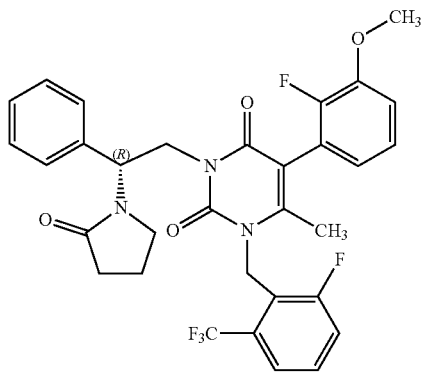

(IIIa) (R-form)

when measured after storage of the tablet for a period of 3 months at a temperature of about 40° C. and at about 75 percent relative humidity.

Embodiment 14. The tablet of any of Embodiments 10-12, wherein the tablet comprises less than about 0.2 weight percent of an elagolix sodium degradation product according to Formula (III)

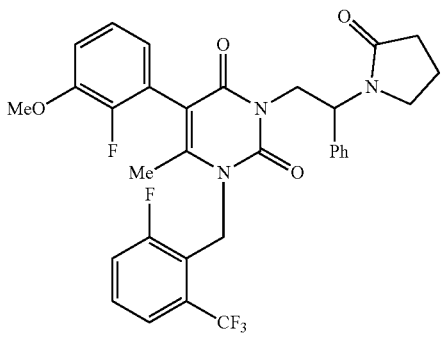 [SMILES: COc1cccc(-c2c(C)n(Cc3c(F)cccc3C(F)(F)F)c(=O)n(CC(c3ccccc3)N3CCCC3=O)c2=O)c1F]

(III), in particular the R-form:

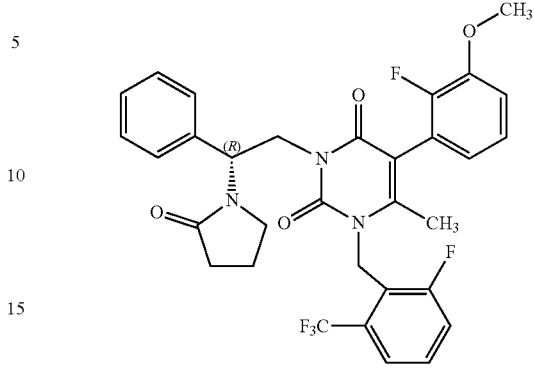

(IIIa) (R-form)

when measured after storage of the tablet for a period of 6 months at a temperature of about 40° C. and at about 75 percent relative humidity.

Embodiment 15. The tablet of any of Embodiments 10-14, wherein at least 75 percent of the elagolix sodium is released from the tablet within 45 minutes when subjected to dissolution testing in a 0.05 M phosphate buffer at a pH of about 6.8.

Embodiment 16. The tablet of any of Embodiments 10-14, wherein at least 75 percent of the elagolix sodium is released from the tablet within 45 minutes when subjected to dissolution testing in a 0.1 M HCl at a pH of about 1.2.

Embodiment 17. A method for preparing a tablet core, comprising the steps of:

i). mixing elagolix sodium, magnesium oxide, at least one disintegrating agent, and optionally at least one additional excipient to provide a tableting mixture;

ii). forming a tablet core by direct compression of the tableting mixture; and iii). optionally, film-coating the tablet core.

Embodiment 18. A method for preparing a tablet core, comprising the steps of:

i). preparing a granulation mixture comprising elagolix sodium, magnesium oxide, at least one disintegrating agent, and optionally at least one additional excipient;

ii). blending the granulation mixture with an extragranular composition which comprises at least a lubricant and disintegrant, to provide a tableting mixture; and iii). forming a tablet core from the tableting mixture; and iv). optionally, film-coating the tablet core.

Embodiment 19. The method of Embodiment 18, wherein the granulation mixture is prepared in a water-free process.

Embodiment 20. A method of treatment of a patient suffering from endometriosis-associated pain or uterine fibroids comprising administering to the patient an effective dose of a pharmaceutical formulation according to any of Embodiments 1-8, an oral dosage form according to Embodiment 9, or a tablet according to Embodiment 10.

Embodiment 21. Use of a pharmaceutical formulation according to any of Embodiments 1-8, an oral dosage form according to Embodiment 9, or a tablet according to Embodiment 10 for treating endometriosis-associated pain or uterine fibroids.

Additionally, the following embodiments, based on the respectively indicated Examples, are described:

Based on Example 1B, and Example 3

In one embodiment, the pharmaceutical formulation, which is a tablet, comprises or consists of:
- elagolix sodium in an amount from 30 weight percent to 40 weight percent, based on the total weight of the formulation;
- magnesium oxide in an amount from 15 weight percent to 20 weight percent, based on the total weight of the formulation;
- and at least one disintegrating agent selected from the group consisting of crospovidone, croscarmellose sodium, sodium starch glycolate, pregelatinized starch, and mixtures thereof in an amount from 15 to 40 weight percent, preferably from 15 to 30 weight percent, based on the total weight of the formulation, and
- mannitol in an amount from 17 weight percent to 30 weight percent, based on the total weight of the formulation; and
- optionally one or more binders, preferably povidone, from 1 weight percent to 5 weight percent, based on the total weight of the formulation and
- at least one lubricant, preferably magnesium stearate, in an amount from 1 weight percent to-5 weight percent, based on the total weight of the formulation.

In this embodiment, the pharmaceutical formulation is preferably obtained by direct compression or dry/wet granulation, wherein the dry granulation preferably includes a slugging step. According to the invention, in the slugging step, the mixed ingredients are compressed into slugs using a tablet press (see Examples 1, 3), preferably having a diameter of at least 10 mm. The slugs are then milled and, after addition of lubricant, are compressed into the final tablets. In all embodiments described herein, a preferred compression pressure during slugging is 15-30 kN; a preferred compression pressure during slugging is: 20-25 kN; and the preferred particle size distribution of the granules after milling the slugs is: not more than (NMT): Diameter 90-300 Microns.

In all embodiments described herein, the preferred tableting pressure for direct compression or compression of granulate (extra- and intragranular phase) is 10-25 kN.

Based on Example 1B, and Example 3

In one embodiment, the pharmaceutical formulation, which is a tablet, comprises
- elagolix sodium in an amount from 30 weight percent to 40 weight percent, based on the total weight of the formulation;
- magnesium oxide in an amount from 15 weight percent to 20 weight percent, based on the total weight of the formulation; and
- at least one disintegrating agent selected from the group consisting of crospovidone, croscarmellose sodium, sodium starch glycolate, pregelatinized starch, and mixtures thereof in an amount from 15 to 40 weight percent, preferably from 15 to 30 weight percent, based on the total weight of the formulation, and
- mannitol in an amount from 10 weight percent to 25 weight percent, based on the total weight of the formulation; and
- one or more binders, preferably one of the binders is povidone, in an amount from 1 weight percent to 8 weight percent, based on the total weight of the formulation and
- optionally colloidal silica anhydrous and/or magnesium stearate in an amount from 1 weight percent to 9 weight percent, based on the total weight of the formulation. In this embodiment, the pharmaceutical formulation is preferably obtained by wet granulation (see Example 2, 7).

Based on Example 1B

In one embodiment, the direct compression formulation, which is a tablet, preferably a tablet of 600 mg without coating, consists of the following ingredients, wherein the "optional additional ingredients" are preferably 0 mg:

| Direct Compression Formulations | | | |
|---|---|---|---|
| Raw Material | mg/tab | mg/tab | mg/tab |
| Elagolix sodium | 190-220 | 190-220 | 190-220 |
| Mannitol | 120-160 | 120-160 | 120-160 |
| Croscarmellose sodium | 100-140 | — | — |
| Sodium starch Glycolate | — | 100-140 | — |
| Crospovidone | — | — | 100-140 |
| Povidone | 10-30 | 10-30 | 10-30 |
| Magnesium Aluminum silicate | — | — | — |
| Magnesium oxide | 80-125 | 80-125 | 80-125 |
| Magnesium stearate | 5-18 | 5-18 | 5-18 |
| Optional additional ingredients | 0-80 | 0-80 | 0-80 |

In one embodiment, the direct compression formulation, which is a tablet, preferably a tablet of 600 mg without coating, consists of the following ingredients, wherein the "optional additional ingredients" are preferably 0 mg:

| Direct Compression Formulations | |
|---|---|
| Raw Material | mg/tab |
| Elagolix sodium | 190-220 |
| Mannitol | 120-160 |
| at least one disintegrating agent selected from the group consisting of crospovidone, croscarmellose sodium, sodium starch glycolate, pregelatinized starch, and mixtures thereof | 100-140 |
| at least one binder, preferably including povidone | 10-30 |
| Magnesium oxide | 80-125 |
| at least one lubricant, preferably including magnesium stearate | 5-18 |
| Optional additional ingredients | 0-80 |

In one embodiment, the direct compression formulation, which is a tablet, consists of the following ingredients, wherein the "optional additional ingredients" are preferably 0%:

| Direct Compression Formulations | |
|---|---|
| Raw Material | % |
| Elagolix sodium | 30-40 |
| Mannitol | 20-30 |

-continued

| Direct Compression Formulations | |
|---|---|
| Raw Material | % |
| at least one disintegrating agent selected from the group consisting of crospovidone, croscarmellose sodium, sodium starch glycolate, pregelatinized starch, and mixtures thereof | 16-25 |
| at least one binder, preferably including povidone | 1-5 |
| Magnesium oxide | 13-21 |
| at least one lubricant, preferably including magnesium stearate | 0.5-5 |
| Optional additional ingredients | 0-up to 100 |

Based on Example 2:

According to another embodiment, the pharmaceutical formulation, which is a tablet, contains granules which include:
- elagolix sodium in an amount from 30 weight percent to 40 weight percent, based on the total weight of the formulation;
- magnesium oxide in an amount from 15 weight percent to 20 weight percent based on the total weight of the formulation;
- at least one disintegrating agent selected from the group consisting of crospovidone, croscarmellose sodium, sodium starch glycolate, pregelatinized starch, and mixtures thereof in an amount from 7 to 20 weight percent, preferably from 7 to 15 weight percent, based on the total weight of the formulation, and
- one or more binders, preferably one of the binders is low hydroxypropyl cellulose, in an amount from 1 weight percent to 8 weight percent, based on the total weight of the formulation, and optionally at least one additional excipient, and
- at least one glidant, e.g. colloidal silica, in an amount from 1 weight percent to 8 weight percent, based on the total weight of the formulation; and wherein said granules are in admixture with an extragranular composition comprising:
- mannitol in an amount from 10 weight percent to 25 weight percent, based on the total weight of the formulation;
- at least one lubricant, preferably magnesium stearate, an amount from 1 weight percent to 5 weight percent, based on the total weight of the formulation; and
- at least one disintegrating agent selected from the group consisting of crospovidone, croscarmellose sodium, sodium starch glycolate, pregelatinized starch, and mixtures thereof in an amount from 7 to 20 weight percent, based on the total weight of the formulation, to provide the tablet formulation.

In one embodiment, the tablet, which is preferably a tablet of 600 mg without coating, consists of the following ingredients:

| Fluid Bed Granulation Formulation | |
|---|---|
| Raw Material | mg/tab |
| Intragranular | |
| Elagolix sodium | 190-220 |
| Magnesium oxide | 80-125 |

| Fluid Bed Granulation Formulation | |
|---|---|
| Raw Material | mg/tab |
| Crospovidone | 40-80 |
| Low hydroxypropyl cellulose | 15-35 |
| Colloidal silica anhydrous | 5-20 |
| Optional additional ingredients | 0-40 |
| Extragranular | |
| Mannitol | 120-160 |
| Sodium starch Glycolate | 10-30 |
| Crospovidone | 40-80 |
| Magnesium stearate | 5-20 |
| Optional additional ingredients | 0-40 |

In one embodiment, the tablet, which is preferably a tablet of 600 mg without coating, consists of the following ingredients:

| Fluid Bed Granulation Formulation | |
|---|---|
| Raw Material | mg/tab |
| Intragranular | |
| Elagolix sodium | 190-220 |
| Magnesium oxide | 80-125 |
| at least one disintegrating agent selected from the group consisting of crospovidone, croscarmellose sodium, sodium starch glycolate, pregelatinized starch, and mixtures thereof | 40-80 |
| at least one binder, preferably including low hydroxypropyl cellulose | 15-35 |
| at least one glidant, preferably including colloidal silica anhydrous | 0-20 |
| Optional additional ingredients | 0-40 |
| Extragranular | |
| Mannitol | 120-160 |
| at least one disintegrating agent selected from the group consisting of crospovidone, croscarmellose sodium, sodium starch glycolate, pregelatinized starch, and mixtures thereof | 40-110 |
| Magnesium stearate | 5-20 |
| Optional additional ingredients | 0-40 |

In one embodiment, the tablet, which is preferably a tablet of 600 mg without coating, consists of the following ingredients:

| Fluid Bed Granulation Formulation | |
|---|---|
| Raw Material | % |
| Intragranular | |
| Elagolix sodium | 30-40 |
| Magnesium oxide | 13-21 |
| at least one disintegrating agent selected from the group consisting of crospovidone, croscarmellose sodium, sodium starch glycolate, pregelatinized starch, and mixtures thereof | 7-14 |
| at least one binder, preferably including low hydroxypropyl cellulose | 2-6 |
| at least one glidant, preferably including colloidal silica anhydrous | 0-4 |
| Optional additional ingredients | 0-10 |

-continued

| Fluid Bed Granulation Formulation | |
|---|---|
| Raw Material | % |
| Extragranular | |
| Mannitol | 20-30 |
| at least one disintegrating agent selected from the group consisting of crospovidone, croscarmellose sodium, sodium starch glycolate, pregelatinized starch, and mixtures thereof | 7-20 |
| Magnesium stearate | 0.5-5 |
| Optional additional ingredients | 0-10 |

Based on Example 3:

In one embodiment, the formulation, which is a tablet, preferably a tablet of 600 mg without coating, consists of the following ingredients, wherein the "optional additional ingredients" are preferably 0 mg:

| Dry Granulation Formulations | |
|---|---|
| Raw Material | mg/tab |
| Intragranular | |
| Elagolix sodium | 190-220 |
| Mannitol | 120-160 |
| Crospovidone | 100-140 |
| Povidone | 10-30 |
| Magnesium oxide | 80-125 |
| Magnesium stearate | 0-20 |
| Optional additional ingredients | 0-40 |
| Extragranular | |
| Magnesium stearate | 5-20 |
| Optional additional ingredients | 0-40 |

Manufacture by use of slugging

In one embodiment, the formulation, which is a tablet, preferably a tablet of 600 mg without coating, comprises or consists of the following ingredients, wherein the "optional additional ingredients" are preferably 0 mg:

| Dry Granulation Formulations | |
|---|---|
| Raw Material | mg/tab |
| Intragranular | |
| Elagolix sodium | 190-220 |
| Mannitol | 120-160 |
| at least one disintegrating agent selected from the group consisting of crospovidone, croscarmellose sodium, sodium starch glycolate, pregelatinized starch, and mixtures thereof | 100-140 |
| binder, preferably povidone | 10-30 |
| Magnesium oxide | 80-125 |
| lubricant, preferably magnesium stearate | 0-20 |
| Optional additional ingredients | 0-40 |
| Extragranular | |
| lubricant, preferably magnesium stearate | 5-20 |
| Optional additional ingredients | 0-40 |

In a preferred embodiment, the formulation is prepared by use of slugging.

In one embodiment, the formulation, which is a tablet, comprises or consists of the following ingredients, wherein the "optional additional ingredients" are preferably 0%:

| Dry Granulation Formulations | |
|---|---|
| Raw Material | % |
| Intragranular | |
| Elagolix sodium | 30-40 |
| Mannitol | 20-30 |
| at least one disintegrating agent selected from the group consisting of crospovidone, croscarmellose sodium, sodium starch glycolate, pregelatinized starch, and mixtures thereof | 17-25 |
| binder, preferably povidone | 1-5 |
| Magnesium oxide | 13-21 |
| lubricant, preferably magnesium stearate | 0-4 |
| Optional additional ingredients | 0-10 |
| Extragranular | |
| lubricant, preferably magnesium stearate | 0.5-5 |
| Optional additional ingredients | 0-up to 100 |

Manufacture by use of slugging

Based on Example 6

In one embodiment, the formulation, which is a tablet, preferably a tablet of 600 mg without coating, consists of the following ingredients, wherein the "optional additional ingredients" are preferably 0 mg:

| Dry Granulation Formulations | |
|---|---|
| Raw Material | mg/tab |
| Intragranular | |
| Elagolix sodium | 190-220 |
| Crospovidone | 100-140 |
| Povidone | 10-30 |
| Magnesium oxide | 80-125 |
| Optional additional ingredients | 0-40 |
| Extragranular | |
| Mannitol | 120-160 |
| Magnesium stearate | 5-20 |
| Optional additional ingredients | 0-40 |

Manufacture by use of slugging

In one embodiment, the formulation, which is a tablet, preferably a tablet of 600 mg without coating, comprises or consists of the following ingredients, wherein the "optional additional ingredients" are preferably 0 mg:

| Dry Granulation Formulations | |
|---|---|
| Raw Material | mg/tab |
| Intragranular | |
| Elagolix sodium | 190-220 |
| at least one disintegrating agent selected from the group consisting of crospovidone, croscarmellose sodium, sodium starch | 100-140 |

-continued

| Dry Granulation Formulations | |
|---|---|
| Raw Material | mg/tab |
| glycolate, pregelatinized starch, and mixtures thereof | |
| Binder, preferably povidone | 10-30 |
| Magnesium oxide | 80-125 |
| Optional additional ingredients | 0-40 |
| Extragranular | |
| Mannitol | 120-160 |
| lubricant, preferably magnesium stearate | 5-20 |
| Optional additional ingredients | 0-40 |

Manufacture by use of slugging

In one embodiment, the formulation comprises or consists of the following ingredients, wherein the "optional additional ingredients" are preferably 0%:

| Dry Granulation Formulations | |
|---|---|
| Raw Material | % |
| Intragranular | |
| Elagolix sodium | 30-40 |
| at least one disintegrating agent selected from the group consisting of crospovidone, croscarmellose sodium, sodium starch glycolate, pregelatinized starch, and mixtures thereof | 16-25 |
| Binder, preferably povidone | 1-5 |
| Magnesium oxide | 13-21 |
| Optional additional ingredients | 0-10 |
| Extragranular | |
| Mannitol | 20-30 |
| lubricant, preferably magnesium stearate | 0.5-5 |
| Optional additional ingredients | 0-10 |

Manufacture by use of slugging

Based on Example 4A and Example 7:

In one embodiment, the tablet, preferably a tablet of 600 mg without coating, consists of the following ingredients:

| (Wet Granulation Formulation) | | | |
|---|---|---|---|
| Raw Material | mg/tab | mg/tab | mg/tab |
| Intragranular | | | |
| Mannitol | 120-160 | 120-160 | 80-120 |
| Magnesium oxide | 50-90 | 50-90 | 50-90 |
| Crospovidone | — | — | 50-70 |
| Sodium starch glycolate | 50-70 | — | — |
| Croscarmellose sodium | — | 50-70 | — |
| Purified water | qs | qs | qs |
| Optional additional ingredients | 0-40 | 0-40 | 0-40 |
| Extragranular | | | |
| Elagolix Sodium | 190-220 | 190-220 | 190-220 |
| Magnesium oxide | 25-50 | 25-50 | 25-50 |
| Povidone | 15-30 | 15-30 | — |
| Low hydroxy propylcellulose | — | — | 15-35 |
| Crospovidone | — | — | 50-70 |
| Sodium starch glycolate | 50-70 | — | 20-40 |
| Croscarmellose sodium | — | 50-70 | — |
| Magnesium stearate | 4-8 | 4-8 | 4-14 |
| Optional additional ingredients | 0-40 | 0-40 | 0-40 |

In one embodiment, the tablet, preferably a tablet of 600 mg without coating, consists of the following ingredients:

| (Wet Granulation Formulation) | |
|---|---|
| Raw Material | mg/tab |
| Intragranular | |
| Mannitol | 80-160 |
| Magnesium oxide | 50-90 |
| at least one disintegrating agent selected from the group consisting of crospovidone, croscarmellose sodium, sodium starch glycolate, pregelatinized starch, and mixtures thereof | 50-70 |
| Purified water | qs |
| Optional additional ingredients | 0-40 |
| Extragranular | |
| Elagolix Sodium | 190-220 |
| Magnesium oxide | 25-50 |
| at least one binder, preferably including low hydroxy propylcellulose | 15-30 |
| at least one disintegrating agent selected from the group consisting of crospovidone, croscarmellose sodium, sodium starch glycolate, pregelatinized starch, and mixtures thereof | 50-70 |
| at least one lubricant preferably including magnesium stearate | 4-8 |
| Optional additional ingredients | 0-40 |

In one embodiment, the tablet, preferably a tablet of 600 mg without coating, consists of the following ingredients:

| (Wet Granulation Formulation) | |
|---|---|
| Raw Material | % |
| Intragranular | |
| Mannitol | 13-30 |
| Magnesium oxide | 8-15 |
| at least one disintegrating agent selected from the group consisting of crospovidone, croscarmellose sodium, sodium starch glycolate, pregelatinized starch, and mixtures thereof | 8-12 |
| Purified water | qs |
| Optional additional ingredients | 0-10 |
| Extragranular | |
| Elagolix Sodium | 30-40 |
| Magnesium oxide | 4-9 |
| at least one binder, preferably including low hydroxy propylcellulose | 2-5 |
| at least one disintegrating agent selected from the group consisting of crospovidone, croscarmellose sodium, sodium starch glycolate, pregelatinized starch, and mixtures thereof | 8-12 |
| at least one lubricant preferably including magnesium stearate | 0.4-5 |
| Optional additional ingredients | 0-10 |

Based on Example 4C

In the below examples, the tablet is prepared by using a wet granulation method, wherein the granulation liquid comprises non-aqueous solvent(s) and is water-free. Preferred non-aqueous solvents include dichloromethane, ethanol, isopropanol, acetone, and mixtures thereof, more preferably the non-aqueous solvents include acetone and dichloromethane, and mixtures thereof. Most preferably, the non-aqueous solvent is dichloromethane.

In one embodiment, the tablet, preferably a tablet of 600 mg without coating, consists of the following ingredients:

| Wet Granulation Formulations | |
|---|---|
| Raw Material | mg/tab |
| Intragranular | |
| Elagolix sodium | 190-220 |
| Mannitol | 80-120 |
| Crospovidone | 50-70 |
| Magnesium oxide | 80-120 |
| Sodium starch Glycolate | 10-30 |
| Colloidal silica anhydrous | 5-20 |
| Low hydroxypropyl cellulose | 15-35 |
| Optional additional ingredients | 0-40 |
| Extragranular | |
| Crospovidone | 50-70 |
| Magnesium stearate | 5-20 |
| Optional additional ingredients | 0-40 |

In one embodiment, the tablet, preferably a tablet of 600 mg without coating, consists of the following ingredients:

| Wet Granulation Formulations | |
|---|---|
| Raw Material | mg/tab |
| Intragranular | |
| Elagolix sodium | 190-220 |
| Mannitol | 80-120 |
| Crospovidone | 50-70 |
| Magnesium oxide | 80-120 |
| at least one disintegrating agent selected from the group consisting of crospovidone, croscarmellose sodium, sodium starch glycolate, pregelatinized starch, and mixtures thereof | 10-30 |
| at least one glidant, preferably including colloidal silica anhydrous | 5-20 |
| at least one binder, preferably including low hydroxypropyl cellulose | 15-35 |
| Optional additional ingredients | 0-40 |
| Extragranular | |
| at least one disintegrating agent selected from the group consisting of crospovidone, croscarmellose sodium, sodium starch glycolate, pregelatinized starch, and mixtures thereof | 50-70 |
| at least one lubricant, preferably including magnesium stearate | 5-20 |
| Optional additional ingredients | 0-40 |

In one embodiment, the tablet consists of the following ingredients:

| Wet Granulation Formulations | |
|---|---|
| Raw Material | % |
| Intragranular | |
| Elagolix sodium | 30-40 |
| Mannitol | 12-20 |
| Crospovidone | 8-12 |
| Magnesium oxide | 13-20 |
| at least one disintegrating agent selected from the group consisting of crospovidone, croscarmellose sodium, sodium starch glycolate, pregelatinized starch, and mixtures thereof | 1-5 |
| at least one glidant, preferably including colloidal silica anhydrous | 5-20 |
| at least one binder, preferably including low hydroxypropyl cellulose | 0.5-5 |
| Optional additional ingredients | 0-10 |
| Extragranular | |
| at least one disintegrating agent selected from the group consisting of crospovidone, croscarmellose sodium, sodium starch glycolate, pregelatinized starch, and mixtures thereof | 8-12 |
| at least one lubricant, preferably including magnesium stearate | 0.5-5 |
| Optional additional ingredients | 0-10 |

EXAMPLES

The following non-limiting examples illustrate various additional aspects of the invention. Unless otherwise indicated, temperatures are in degrees Celsius and percentages are by weight based on the dry weight of the formulation.

Examples 1-4: Preparation of Elagolix Sodium Tablets and Tablet Sink Time Testing A series of elagolix sodium formulations were prepared and tableted using a multiple tableting techniques. Each of the tablets was then tested to determine its Tablet Sink Time.

The method used for determination of Tablet Sink Time is in accordance with United States Pharmacopeia (USP) Chapter 701 (Disintegration). According to this method, the Tablet Sink Time is the residence time taken by the formulation before its erosion and passage through a mesh screen with an aperture of size 1.8-2.2 mm and a wire diameter of 0.570-0.660 mm, when agitated in an acidic media by an apparatus with an up and down motion.

The disintegration apparatus used for this testing contains 6 baskets, each made of wire mesh of the specified size and opening. For the test, each of the tablets was placed in wire basket in a media having a pH of about 1.2. The baskets are then moved up & down within the acid media to disintegrate the tablet and release the shredded parts into the media through the wire mesh. The time required for this disintegration and release is measured for each tablet and recorded as the Tablet Sink Time. A Tablet Sink Time of less 35 minutes is considered satisfactory.

EXAMPLE 1. In this Example, a series of elagolix sodium formulations were
prepared and tableted using a direct compression tableting technique. In general, the manufacturing procedure for each tablet was as follows:
1. Elagolix and a dispersing agent were both screened through a 0.4 mm mesh.
2. The aforementioned ingredient together with all remaining components except magnesium stearate lubricant were then screened together through a 0.4 mm mesh.
3. Magnesium stearate, which had been previously screened through a 0.25 mm mesh was then mixed in blender with the screened drug mixture from step 2.

4. The lubricated blend was then compressed into tablets in a tableting press with a compression force of 3-20 kN (kilo Newton), and an ejection energy <3 Joules with ejection time less than 200 milliseconds.

The make-up and measured Tablet Sink Times of the tablets prepared in this example were as follows:

| EXAMPLE-1A (Direct Compression Formulations) | | | | | | | | | |
|---|---|---|---|---|---|---|---|---|---|
| | Raw Material mg/tablet (mg/tab) | | | | | | | | |
| Elagolix sodium | 207 | 207 | 207 | 207 | 207 | 207 | 207 | 207 | 207 |
| Mannitol | 200.3 | 200.3 | 200.3 | 200.3 | 200.3 | 229.0 | 139.4 | 139.4 | 139.4 |
| Pregelatinized starch | 59.1 | 59.1 | 59.1 | 59.1 | 59.1 | 59.0 | — | — | — |
| Croscarmellose sodium | — | — | — | — | — | — | — | — | — |
| Sodium starch Glycolate | — | — | — | — | — | — | — | — | — |
| Crospovidone | — | — | — | — | — | — | 120 | 120 | 120 |
| Povidone | 18.4 | 18.4 | 18.4 | 18.4 | 18.4 | 20.0 | 18.4 | 18.4 | 18.4 |
| Magnesium Aluminum silicate | — | — | — | — | — | 70 | — | — | — |
| Sodium carbonate monohydrate | — | — | — | — | 104 | — | — | — | — |
| Calcium silicate | 104 | — | — | — | — | — | — | — | — |
| Calcium carbonate | — | 104 | — | — | — | — | — | — | — |
| Calcium acetate | — | — | 104 | — | — | — | — | — | — |
| Magnesium oxide | — | — | — | 104 | — | — | — | — | — |
| Magnesium Carbonate | — | — | — | — | — | — | — | — | 104 |
| Meglumine | — | — | — | — | — | — | 104 | — | — |
| Sodium chloride | — | — | — | — | — | — | — | 104 | — |
| Magnesium stearate | 11.2 | 11.2 | 11.2 | 11.2 | 11.2 | 15.0 | 11.2 | 11.2 | 11.2 |
| Tablet weight | 600 | 600 | 600 | 600 | 600 | 600 | 600 | 600 | 600 |
| Tablet Sink Time (min) | >60 | >60 | >60 | >60 | 35 | >42 | 43 | >60 | >60 |

| EXAMPLE-1B (Direct Compression Formulations) | | | | | | | | |
|---|---|---|---|---|---|---|---|---|
| Raw Material | mg/tab | mg/tab | mg/tab | mg/tab | mg/tab | mg/tab | mg/tab | mg/tab |
| Elagolix sodium | 207 | 207 | 207 | 207 | 207 | 207 | 207 | 207 |
| Mannitol | 139.4 | 139.4 | 139.4 | 243.4 | 243.4 | 243.4 | 243.4 | 243.4 |
| Croscarmellose sodium | 120 | — | — | 120 | — | — | 60 | — |
| Sodium starch Glycolate | — | 120 | — | — | 120 | — | 60 | 60 |
| Crospovidone | — | — | 120 | — | — | 120 | — | 60 |
| Povidone | 18.4 | 18.4 | 18.4 | 18.4 | 18.4 | 18.4 | 18.4 | 18.4 |
| Magnesium Aluminum silicate | — | — | — | — | — | — | — | — |
| Magnesium oxide | 104 | 104 | 104 | — | — | — | — | — |
| Magnesium stearate | 11.2 | 11.2 | 11.2 | 11.2 | 11.2 | 11.2 | 11.2 | 11.2 |
| Tablet weight (mg) | 600 | 600 | 600 | 600 | 600 | 600 | 600 | 600 |
| Tablet Sink Time (min.) | 15 | 27 | 18 | 57 | >60 | 48 | >60 | >60 |

EXAMPLE 2. In this Example, a series of elagolix sodium formulations were prepared and tableted using a fluid bed granulation technique. In general, the manufacturing procedure for each tablet was as follows:

1. A granulating liquid was prepared by dissolving a dispersing agent under slow stirring, in either purified water, or alternatively in a non-aqueous solvent (di-chloromethane).
2. A raw material bed containing elagolix sodium and all other components except a lubricant was prepared. The elagolix sodium in the bed was previously screened through a 0.4 mm mesh screen.
3. The granulating liquid was then sprayed over the screened raw material bed in a fluid bed dryer to provide a granulated bed. In some instances, additional extragranular elagolix sodium was also added over the granulated bed.
4. The granulated bed, with either purified water or a non-aqueous solvent, was then dried and screened through a 0.6 mm mesh screen.
5. Magnesium stearate, which had been previously screened through a 0.25 mm mesh was then mixed in blender with the screened drug mixture from step 4.
6. The lubricated blend was then compressed into tablets in a tableting press with a compression force of 3-20 kN, and an ejection energy <3 Joules with ejection time less than 200 milliseconds.

The make-up of the tablets prepared in this example were as follows:

| EXAMPLE-2 (Fluid Bed Granulation Formulations) | | | | | | | |
|---|---|---|---|---|---|---|---|
| Raw Material | mg/tab | mg/tab | mg/tab | mg/tab | mg/tab | mg/tab | mg/tab |
| Intragranular | | | | | | | |
| Elagolix sodium | 207 | 207 | 207 | 207 | 207 | 207 | 207 |
| Sodium hydroxide | 20 | 20 | 20 | 20 | 20 | 20 | — |
| Magnesium oxide | — | — | — | — | — | — | 104 |
| Crospovidone | — | — | — | — | — | — | 60 |
| Low hydroxypropyl cellulose | — | — | — | — | — | — | 24 |
| Colloidal silica anhydrous | — | — | — | — | — | — | 12 |
| Purified water | qs | qs | qs | qs | qs | qs | — |
| Dichloromethane | — | — | — | — | — | — | qs |
| Extragranular | | | | | | | |
| Mannitol | 284.3 | 223.4 | 223.4 | 223.4 | 223.4 | 223.4 | 103.0 |
| Povidone | 18.4 | 18.4 | 18.4 | 18.4 | 18.4 | 18.4 | — |
| Pregelatinized starch | 59.1 | — | — | — | — | — | — |
| Croscarmellose sodium | — | 120 | — | — | — | 60 | — |
| Sodium starch Glycolate | — | — | 120 | — | 60 | — | 18.00 |
| Crospovidone | — | — | — | 120 | 60 | 60 | 60 |
| Magnesium stearate | 11.2 | 11.2 | 11.2 | 11.2 | 11.2 | 11.2 | 11.2 |
| Tablet weight (mg) | 600 | 600 | 600 | 600 | 600 | 600 | 600 |
| Tablet Sink Time (min.) | >60 | 58 | 52 | 52 | 56 | >60 | 28 |

"qs" stands for "quantum sufficit" ("quantity sufficient") and means "amount that is enough". It means that the respectively denoted solvents will be added during manufacturing process for processing of particular manufacturing step. The respective solvents are not present in the final dosage form (tablets), except in trace amounts.

EXAMPLE 3. In this Example, a series of elagolix sodium formulations were prepared and tableted using a dry granulation tableting technique. In general, the manufacturing procedure for each tablet was as follows:

1. Elagolix and a dispersing agent were both screened through a 0.4 mm mesh.
2. The aforementioned ingredient together with all remaining components except magnesium stearate lubricant were then screened together through a 0.4 mm mesh.
3. Magnesium stearate, which had been previously screened through a 0.25 mm mesh was then mixed in blender with the screened drug mixture from step 2.
4. The lubricated blend was then either compressed into slugs using a tablet press or compacted into ribbons using a roller compactor.
5. The slugs or ribbons from step 4 were then milled and screened through a 0.6 mm mesh screen. The screened mixture was then mixed in a blender with additional magnesium stearate lubricant. The lubricant had previously been screened through a 0.25 mm mesh screen.
6. The lubricated blend from step 5 was then compressed into tablets in a tableting press with a compression force of 3-20 kN, and an ejection energy <3 Joules with ejection time less than 200 milliseconds.

The make-up of the tablets prepared in this example were as follows:

| EXAMPLE-3 (Dry Granulation Formulations) | | | | |
|---|---|---|---|---|
| Raw Material | mg/tab | mg/tab | mg/tab | mg/tab |
| Intragranular | | | | |
| Elagolix sodium | 207 | 207 | 207 | 207 |
| Mannitol | 139.4 | 139.4 | 139.4 | 58 |
| Dicalcium phosphate | — | — | — | 72 |
| Crospovidone | 120 | 120 | — | 84 |
| Sodium starch Glycolate | — | — | 120 | — |
| Povidone | 18.4 | 18.4 | 18.4 | 24 |
| Magnesium oxide | 104 | 104 | 104 | 60 |
| Calcium carbonate | — | — | — | 84 |
| Magnesium stearate | 5.2 | 5.2 | 5.2 | 5.0 |
| Extragranular | | | | |
| Magnesium stearate | 6 | 6 | 6 | 6 |
| Tablet weight | 600 | 600 | 600 | 600 |
| Tablet Sink Time (mm.) | 30 | >60 | 58 | >60 |
| Manufacture by use of | slugging | roller compactor | roller compactor | roller compactor |

EXAMPLE 4. In this Example, a series of elagolix sodium formulations were prepared and tableted using a wet granulation technique. In general, the manufacturing procedure for each tablet was as follows:

1. Dispersing agent with elagolix or without elagolix, and other excipients (except a lubricant) were screened through a 0.4 mm mesh screen.
2. Purified water or a non-aqueous solvent or dispersing agent dispersed in purified water was used a granulating liquid. This granulating liquid with either sprayed (Example 4C) or poured over a raw material bed (Example 4A and Example 4B) of the screened mixture from step 1 in a high shear granulator. In some instances, additional extragranular elagolix sodium was also added over the granulated bed.
3. The granulated bed, with either purified water or a non-aqueous solvent, was then dried and screened through a 0.6 mm mesh.
4. Magnesium stearate, which had been previously screened through a 0.25 mm mesh was then mixed in blender with the screened drug mixture from step 3.
5. The lubricated blend was then compressed into tablets in a tableting press with a compression force of 3-20 kN, and an ejection energy <3 Joules with ejection time less than 200 milliseconds.

The make-up of the tablets prepared in this example were as follows:

| EXAMPLE-4A (Wet Granulation Formulations) | | | | | |
|---|---|---|---|---|---|
| Raw Material | mg/tab | mg/tab | mg/tab | mg/tab | mg/tab |
| Intragranular | | | | | |
| Mannitol | 143.6 | 143.6 | 143.6 | 143.6 | 103 |
| Magnesium oxide | 70.3 | 70.3 | 70.3 | 70.3 | 69.3 |
| Crospovidone | 60 | 60 | — | — | 60.00 |
| Sodium starch glycolate | — | — | 60 | — | — |
| Croscarmellose sodium | — | — | — | 60 | — |
| Purified water | qs | qs | qs | qs | qs |
| Extragranular | | | | | |
| Elagolix Sodium | 207 | 207 | 207 | 207 | 207 |
| Magnesium oxide | 34.7 | 34.7 | 34.7 | 34.7 | 34.7 |
| Povidone | 18.4 | 18.4 | 18.4 | 18.4 | — |
| Low hydroxy propylcellulose | — | — | — | — | 24 |
| Crospovidone | 60.00 | — | — | — | 60 |
| Pregelatinized starch | — | 60 | — | — | — |
| Sodium starch glycolate | — | — | 60 | — | 30 |
| Croscarmellose sodium | — | — | — | 60 | — |
| Magnesium stearate | 6 | 6 | 6 | 6 | 12 |
| Tablet weight (mg) | 600 | 600 | 600 | 600 | 600 |
| Tablet Sink Time (min.) | 50 | >60 | 30 | 30 | 28 |

In this example, Magnesium oxide was dispersed in water and granulated. Then, the wet mass was dried and screened through an appropriate screen. To the screened granules, elagolix sodium and the further excipients were added and compressed.

| EXAMPLE-4B (Wet Granulation Formulations) | | | | |
|---|---|---|---|---|
| Raw Material | mg/tab | mg/tab | mg/tab | mg/tab |
| Intragranular | | | | |
| Mannitol | 143.6 | 143.6 | 144.6 | 144.6 |
| Crospovidone | 60 | 60 | 60 | 60 |
| Potassium hydroxide | 14 | 14 | — | — |
| Meglumine | 12 | 12 | 12 | 12 |
| Magnesium aluminum silicate | — | — | 16 | 16 |
| Purified water | qs | qs | qs | qs |
| Extragranular | | | | |
| Elagolix Sodium | 207 | 207 | 207 | 207 |
| Mannitol | 78 | 78 | 62 | 62 |
| Povidone | 18.4 | 18.4 | 18.4 | 18.4 |
| Crospovidone | 60 | — | 60 | — |
| Sodium starch glycolate | — | 60 | — | 60 |
| Magnesium aluminum silicate | — | — | 14 | 14 |
| Magnesium stearate | 6 | 6 | 6 | 6 |
| Tablet weight (mg) | 600 | 600 | 600 | 600 |
| Tablet Sink Time (min) | 45 | 43 | 60 | 60 |

In this example, Potassium hydroxide or Meglumine or Magnesium aluminum silicate were dispersed in water and granulated. Then, the wet mass was dried and screened through an appropriate screen. To the screened granules, elagolix sodium and the further excipients were added and compressed.

| EXAMPLE-4C (Wet Granulation Formulations) | | | |
|---|---|---|---|
| Raw Material | mg/tab | mg/tab | mg/tab |
| Intragranular | | | |
| Elagolix sodium | 207 | 207 | 207 |
| Mannitol | 103 | 103 | 103 |
| Crospovidone | 60 | 60 | 60 |
| Magnesium oxide | 104 | 104 | 104 |
| Sodium starch Glycolate | 18 | 18 | 18 |
| Colloidal silica anhydrous | 12 | 12 | 12 |
| Low hydroxypropyl cellulose | 24 | 24 | 24 |
| Acetone | qs | — | — |
| Dichloromethane | — | qs | — |
| Isopropanol | — | — | qs |
| Extragranular | | | |
| Crospovidone | 60 | 60 | 60 |
| Magnesium stearate | 12 | 12 | 12 |
| Tablet weight (mg) | 600 | 600 | 600 |
| Tablet Sink Time (min.) | 28 | 18 | 41 |

In this example, Magnesium oxide including the API elagolix sodium and other excipients were granulated with acetone, dichloromethane, or isopropanol. Then, the wet mass was dried and screened through an appropriate screen. To the screened granules, the other excipients were added and compressed.

Conclusions from Examples 1 to 4:

From Examples 1-4: In all formulations with magnesium oxide and disintegration agents like croscarmellose sodium, sodium starch glycolate & Crospovidone manufactured with direct compression, fluid bed granulation, dry granulation & wet granulation, the formulation were found to have a tablet sink time of less than 35 min tested in accordance with United States Pharmacopeia (USP) Chapter 701 (Disintegration).

Examples 5-8: Tablet Dissolution Testing

Elagolix sodium formulations were prepared and tableted using different tableting techniques. Each of the tablets was then tested to determine its Tablet Dissolution rate, as well as the Tablet Sink Time.

For tablet dissolution testing, a sample of each tablet was placed in a phosphate buffered media at a pH of about 6.8, and the dissolution of the tablet was measured over time. Dissolution for these samples was measured according to United States Pharmacopeia (USP) Type II (Paddle) apparatus using a speed of 40 rpm in 900 mL of 0.05 M phosphate buffer at a pH of about 6.8. For this test, a dissolution rate of at least 75% within 45 minutes is consider satisfactory.

The method used for determination of Tablet Sink Time is in accordance with United States Pharmacopeia (USP) Chapter 701 (Disintegration), as described above in Examples 1-4. For the Tablet Sink Time test, a sink time of 35 minutes or less is considered satisfactory.

The composition and method of manufacture for each tablet is described below.

EXAMPLE 5. In this example, an elagolix sodium tablet was prepared by direct compression. The method of tablet manufacture was the same as in Example 1 above. The composition of this elagolix sodium tablet was as follows:

| Example-5: Direct compression | |
|---|---|
| Raw Material | mg/tab |
| Elagolix Sodium | 207 |
| Mannitol | 139.4 |
| Magnesium Oxide | 104 |
| Crospovidone | 120 |
| Povidone | 18.4 |
| Magnesium stearate | 11.2 |
| Tablet weight (mg) | 600 |
| Tablet Sink Time (min.) | 18 |

EXAMPLE 6. In this example, an elagolix sodium tablet was prepared by dry granulation. The method of tablet manufacture was the same as in Example 3 above. The composition of this elagolix sodium tablet was as follows:

| Example-6: Dry granulation | |
|---|---|
| Raw Material | mg/tab |
| Intragranular | |
| Elagolix Sodium | 207 |
| Magnesium Oxide | 104 |
| Povidone | 18.4 |
| Crospovidone | 120 |
| Extragranular | |
| Mannitol | 139.4 |
| Magnesium stearate | 11.2 |
| Tablet weight (mg) | 600 |
| Tablet Sink Time (min) | 30 |

EXAMPLE 7. In this example, an elagolix sodium tablet was prepared by aqueous wet granulation. The method of tablet manufacture was the same as in Example 4 above, using aqueous solvent and adding extragranular elagolix sodium and excipients.

The composition of this elagolix sodium tablet was as follows:

| Example-7: Aqueous Wet granulation, with Extragranular API addition | |
|---|---|
| Raw Material | mg/tab |
| Intragranular | |
| Magnesium Oxide | 69.3 |
| Mannitol | 103 |
| Crospovidone | 60 |
| Purified water | qs |
| Extragranular | |
| Elagolix Sodium | 207 |
| Magnesium Oxide | 34.7 |
| Low hydroxy propyl cellulose | 24 |
| Crospovidone | 60 |
| Sodium starch glycolate | 30 |
| Magnesium stearate | 12 |
| Tablet weight (mg) | 600 |
| Tablet Sink Time (min) | 28 |

EXAMPLE 8. In this example, elagolix sodium tablets were prepared by non-aqueous wet granulation at two different strengths: (1) 200 mg elagolix and (2) 150 mg elagolix. The methods of tablet manufacture were the same as in Example 4 above, using a non-aqueous solvent (acetone) and adding extrangranular crospovidone, pregelatinized starch and magnesium stearate. In addition, the tablet cores were film coated after tableting. Specifically, the 150 mg elagolix tablet cores were coated Opadry Purple and the 200 mg elagolix tablet cores were coated with Opadry Pink. Both were coated to a target coating weight of about 2.0 to 3.0% w/w (weight/weight).

The composition of these elagolix sodium tablets was as follows:

| Example-8: Non-Aqueous Wet granulation | | | |
|---|---|---|---|
| | Elagolix dose/tablet | | |
| Raw Material | 200 mg mg/tab | 200 mg mg/tab | 150 mg mg/tab |
| Intragranular | | | |
| Elagolix sodium | 207 | 207 | 155.25 |
| Mannitol | 76 | 106 | 79 |
| Magnesium oxide | 104 | 104 | 78 |
| Crospovidone | 60 | 60 | 45 |
| Low hydroxy propyl cellulose | 24 | 24 | 18 |
| Sodium starch glycolate | 18 | 18 | 13.5 |
| Colloidal silica anhydrous | 12 | 12 | 9 |
| Acetone | qs | qs | qs |
| Extragranular | | | |
| Crospovidone | 60 | 60 | 45.00 |
| Pregelatinized starch | 30 | — | — |
| Magnesium stearate | 9 | 9 | 6.75 |
| Tablet weight | 600 | 600 | 450 |
| Coating layer | | | |
| Opadry Pink | 15 | 15 | — |
| Opadry Purple | — | — | 13.5 |
| Coated Tablet weight (mg) | 615 | 615 | 463.5 |
| Tablet Sink Time (min) | 18 | 20 | 23 |

The measured dissolution rates at pH 1.2 for the tablets were as follows:

| Time (min) | Example 5 - Direct compression | Example 6 - Dry Granulation | Example 7 - Aqueous wet granulation with API EG addition | Example 8 - Non aqueous wet granulation (200 mg) | Example 8 - Non aqueous wet granulation (200 mg) | Example 8 - Non aqueous wet granulation (150 mg) |
|---|---|---|---|---|---|---|
| 5 | 23.0 | 38.6 | 7.8 | 21.9 | 7.7 | 12 |
| 10 | 43.6 | 69.5 | 20.6 | 49.7 | 24.1 | 27.9 |
| 15 | 58.5 | 87 | 33.2 | 72.7 | 42.9 | 43.6 |
| 20 | 68.3 | 94.8 | 45.4 | 91.2 | 59.8 | 58 |
| 30 | 83.5 | 97.8 | 67.2 | 96.3 | 87.9 | 81.8 |
| 45 | 89.1 | 99 | 88.5 | 96.9 | 94.9 | 98 |
| 60 | 89.3 | 98.6 | 93.6 | 97.1 | 96.6 | 100.9 |

Conclusions from Examples 5 to 8:

From this data, it may be seen that all of the formulations manufactured achieved the desired drug release rate of at least 75% within 45 minutes. Moreover, all formulations with magnesium oxide and disintegrating agent like sodium starch glycolate, pregelatinized starch and crospovidone manufactured with direct compression, fluid bed granulation, dry granulation and wet granulation were found to exhibit significant drug release of at least 75% within 45 minutes tested in pH 1.2 and pH 6.8.

Example 9: Tablet Dissolution Testing at pH 1.2 and at pH 6.8

Additional Elagolix sodium formulations were prepared and tableted using different tableting techniques. The tablets were prepared either by direct compression (using the method of Example 1) or by non-aqueous wet granulation (using the method of Example 8).

Each of the tablets was then tested to determine its Tablet Dissolution rate. In general, the dissolution testing procedure was similar to Examples 5-8, except different dissolution media were used. In this example, the tablets were tested using a strong acidic media containing 0.1 M HCl (pH of about 1.2) and in a phosphate buffered media at a pH of about 6.8. As in Examples 5-8, a dissolution rate of at least 75% within 45 minutes is consider satisfactory.

The composition of the elagolix sodium tablets for this example was as follows:

Example-9: Formulations compared for drug release in 0.1M HCl of about pH 1.2 and phosphate buffer of about pH 6.8

| Raw Material | mg/tab | mg/tab | mg/tab | mg/tab |
|---|---|---|---|---|
| Elagolix sodium | 207 | 207 | 207 | 207 |
| Mannitol | 303 | 229 | 106 | 76 |
| Magnesium oxide | — | — | 104 | 104 |
| Crospovidone | 40 | — | 120 | 120 |
| Povidone | 20 | 20 | — | — |
| Pregelatinized starch | — | 59 | — | 30 |
| Low hydroxy propyl cellulose | — | — | 24 | 24 |
| Sodium starch glycolate | — | — | 18 | 18 |
| Magnesium aluminum silicate | — | 70 | — | — |
| Colloidal silica anhydrous | 15 | — | 12 | 12 |
| Magnesium stearate | 15 | 15 | 9 | 9 |
| Acetone | — | — | qs | qs |
| Tablet weight | 600 | 600 | 600 | 600 |
| Tableting Method | Example 1 | Example 1 | Example 8 | Example 8 |
| Formulation name | No dispersing agent | Mg—Al—Silicate | MgO formulation 1 | MgO formulation 2 |

The measured dissolution rates for the tablets were as follows:

Dissolution in 0.1M HCl

| Time (min) | No dispersing agent | Mg—Al—Silicate | MgO formulation 1 | MgO formulation 2 |
|---|---|---|---|---|
| 5 | 4.2 | 2.5 | 5 | 11.3 |
| 10 | 9.4 | 4.7 | 20.1 | 30.5 |
| 15 | 14.4 | 6.6 | 33.6 | 47.2 |
| 20 | 19.1 | 8.7 | 44.8 | 62.3 |
| 30 | 28.1 | 18.6 | 61.7 | 79.9 |
| 45 | 40.3 | 35.6 | 77.1 | 93.1 |
| 60 | 51.2 | 52.9 | 91 | 97.3 |

The drug release in 0.1 M HCl, pH 1.2, is also depicted in FIG. 1.

Dissolution in pH 6.8 Phosphate buffer

| Time (min) | No dispersing agent | Mg—Al—Silicate | MgO formulation 1 | MgO formulation 2 |
|---|---|---|---|---|
| 5 | 23.8 | 13.7 | 12 | 21.9 |
| 10 | 50.3 | 32.6 | 27.9 | 49.7 |
| 15 | 71.4 | 48.4 | 43.6 | 72.7 |
| 20 | 84.9 | 61.4 | 58 | 91.2 |
| 30 | 96.9 | 79.9 | 81.8 | 96.3 |
| 45 | 98.8 | 92.6 | 98 | 96.9 |
| 60 | 98.8 | 95.7 | 100.9 | 97.1 |

Figure 2:
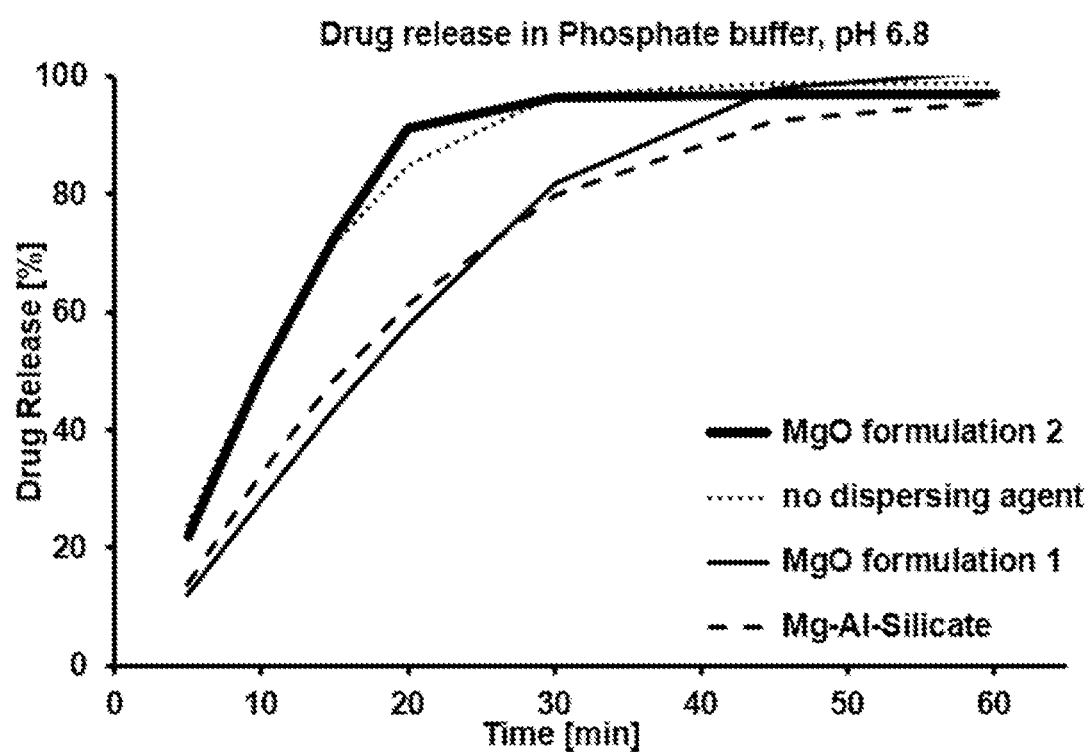
FIG. 2 illustrates the drug release in phosphate buffer, pH 6.8.

The drug release in phosphate buffer, pH 6.8, is also depicted in FIG. 2.

These testing indicate that tablets formulated with Mg—Al-silicate dispersing agent or with no dispersing agent at all may provide acceptable dissolution and release at a buffered pH of about 6.8. However, only the use of a magnesium oxide dispersing agent led to an acceptable dissolution at a strongly acidic pH of about 1.2.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A pharmaceutical formulation comprising:
   elagolix sodium;
   from 10 to 25 weight percent of magnesium oxide, based on the total weight of the formulation; and
   from 15 to 40 weight percent of at least one disintegrating agent, based on the total weight of the formulation,
   wherein said pharmaceutical formulation is a coated tablet and
   wherein the tablet has a Tablet Sink Time of about 35 minutes or less when measured in a 0.1 M HCl at a pH of about 1.2 in accordance with USP Chapter 701 (Disintegration).

2. The pharmaceutical formulation of claim 1, wherein the formulation comprises from 20 weight percent to 50 weight percent of the elagolix sodium based on the total weight of the formulation.

3. The pharmaceutical formulation of claim 1, wherein the formulation comprises at least one disintegrating agent selected from the group consisting of crospovidone, croscarmellose sodium, sodium starch glycolate, pregelatinized starch, and mixtures thereof.

4. The pharmaceutical formulation of claim 1, wherein the formulation comprises crospovidone, sodium starch glycolate, and pregelatinized starch.

5. The pharmaceutical formulation of claim 1, wherein the formulation further comprises at least one excipient selected from the group consisting of sugar alcohols, cellulose derivatives, silica, binders, and lubricants.

6. The pharmaceutical formulation of claim 1, wherein the formulation further comprises at least one excipient selected from the group consisting of mannitol, low-substituted hydroxypropyl cellulose, colloidal silica, povidone, and magnesium stearate.

7. An oral dosage form comprising the pharmaceutical formulation of claim 1.

8. The oral dosage form of claim 7, wherein the tablet comprises from 140 mg to 315 mg of elagolix, in the form of elagolix sodium.

9. The oral dosage form of claim 7, wherein
   the tablet comprises less than 0.10 weight percent of an elagolix sodium degradation product according to Formula III

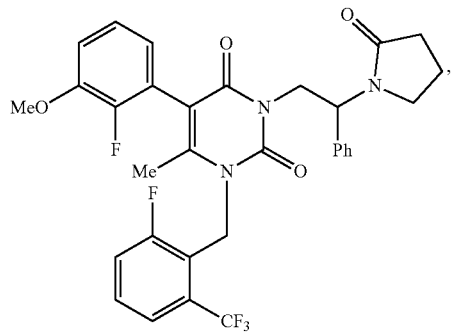

when measured after storage of the tablet for a period of 3 months at a temperature of about 40° C. and at about 75 percent relative humidity.

10. The oral dosage form of claim 7, wherein
    the tablet comprises less than 0.20 weight percent of an elagolix sodium degradation product according to Formula III

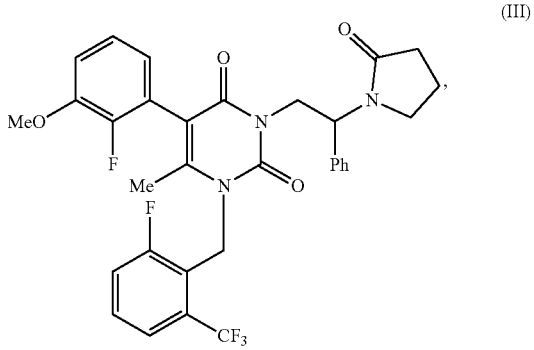 [SMILES: COc1cccc(-c2c(C)n(Cc3c(F)cccc3C(F)(F)F)c(=O)n(CC(c3ccccc3)N3CCCC3=O)c2=O)c1F]

when measured after storage of the tablet for a period of 6 months at a temperature of about 40° C. and at about 75 percent relative humidity.

11. The oral dosage form of claim 7, wherein at least 75 percent of the elagolix sodium is released from the tablet within 45 minutes when subjected to dissolution testing in a 0.05 M phosphate buffer at a pH of about 6.8.

12. The oral dosage form of claim 7, wherein at least 75 percent of the elagolix sodium is released from the tablet within 45 minutes when subjected to dissolution testing in a 0.1 M HCl dissolution solution at a pH of about 1.2.

13. A method for preparing a tablet core, comprising the steps of:
    i). mixing elagolix sodium, magnesium oxide, at least one disintegrating agent, and optionally at least one additional excipient to provide a tableting mixture;
    ii). forming a tablet core by direct compression of the tableting mixture; and
    iii). film-coating the tablet core,
    wherein the tablet has a Tablet Sink Time of about 35 minutes or less when measured in a 0.1 M HCl at a pH of about 1.2 in accordance with USP Chapter 701 (Disintegration).

14. A method for preparing a tablet core, comprising the steps of:
    i). preparing a granulation mixture comprising elagolix sodium, magnesium oxide, at least one disintegrating agent, and optionally at least one additional excipient;
    ii). blending the granulation mixture with an extragranular composition which comprises at least a lubricant and disintegrant, to provide a tableting mixture; and
    iii). forming a tablet core from the tableting mixture, and
    iv). film-coating the tablet core,
    wherein the tablet has a Tablet Sink Time of about 35 minutes or less when measured in a 0.1 M HCl at a pH of about 1.2 in accordance with USP Chapter 701 (Disintegration).

15. The method of claim 14, wherein the granulation mixture is prepared in a water-free process.

16. A method of treatment of a patient suffering from endometriosis-associated pain or uterine fibroids comprising administering to the patient an effective dose of a pharmaceutical formulation according to claim 1.

* * * * *